US012196946B2

(12) United States Patent
Caronia et al.

(10) Patent No.: US 12,196,946 B2
(45) Date of Patent: Jan. 14, 2025

(54) OPHTHALMIC INSTRUMENT EYEPIECE EXTENDER (71) Applicant: Ronald Michael Caronia, Syosset, NY (US)

(72) Inventors: Ronald Michael Caronia, Syosset, NY (US); Edward Allen DeHoog, Long Beach, CA (US)

(73) Assignee: Ronald Michael Corina, Syosset, NY (US)

( * ) Notice: Subject to any disclaimer, the term of this patent is extended or adjusted under 35 U.S.C. 154(b) by 491 days.

(21) Appl. No.: 17/587,182

(22) Filed: Jan. 28, 2022

(65) Prior Publication Data
US 2022/0244523 A1 Aug. 4, 2022

Related U.S. Application Data (60) Provisional application No. 63/143,389, filed on Jan. 29, 2021.

(51) Int. Cl.
G02B 1/00 (2006.01)
A61B 3/12 (2006.01)
A61B 3/135 (2006.01)
G02B 13/00 (2006.01)
G02B 25/00 (2006.01)

(52) U.S. Cl.
CPC .............. G02B 25/001 (2013.01); A61B 3/12 (2013.01); A61B 3/135 (2013.01); G02B 13/0095 (2013.01)

(58) Field of Classification Search
CPC .... G02B 25/001; G02B 13/0095; A61B 3/12; A61B 3/135
See application file for complete search history.

(56) References Cited

U.S. PATENT DOCUMENTS

| | | | |
|---|---|---|---|
| 2,541,014 A | 2/1951 | Orser | |
| 3,848,969 A | 11/1974 | Tajima | |
| 4,353,624 A | 10/1982 | Yonekubo | |
| 4,392,716 A | 7/1983 | Shimizu | |
| 4,396,260 A | 8/1983 | Takizawa et al. | |

(Continued)

FOREIGN PATENT DOCUMENTS

| | | |
|---|---|---|
| CN | 209879123 U | 12/2019 |
| DE | 3811432 C2 | 6/1993 |

(Continued)

OTHER PUBLICATIONS

International Search Report and Written Opinion dated Jun. 7, 2022, received in a corresponding foreign application, 16 pages.

(Continued)

Primary Examiner — James C. Jones
(74) Attorney, Agent, or Firm — Scully, Scott, Murphy & Presser, P.C.

(57) ABSTRACT

The disclosure relates to an eyepiece extender for an ophthalmic microscope, such as a slit lamp microscope. The eyepiece extender comprises certain lens designs and arrangements and provides ergonomic improvement to a user of the ophthalmic microscope and accommodates different magnifications, such as high and low magnifications, while preserving image fidelity for each magnification such that the image is essentially distortion free and color corrected in each magnification instance.

22 Claims, 6 Drawing Sheets (56) References Cited

U.S. PATENT DOCUMENTS

| | | | |
|---|---|---|---|
| 4,676,606 | A | 6/1987 | Takahashi |
| 4,863,250 | A | 9/1989 | Ishizuka |
| 5,097,359 | A | 3/1992 | McKinley |
| 5,991,090 | A | 11/1999 | Strahle |
| 6,476,982 | B1 | 11/2002 | Kawakami |
| 6,485,143 | B2 | 11/2002 | Buettgenbach |
| 7,075,728 | B2 | 7/2006 | Yamaguchi et al. |
| 7,321,474 | B1 | 1/2008 | Jo |
| 7,329,003 | B2 | 2/2008 | Nicolini |
| 7,396,260 | B2 | 7/2008 | Wilk |
| 10,444,484 | B2 | 10/2019 | Nakamura et al. |
| 2008/0079901 | A1 | 4/2008 | Nakamura |
| 2018/0172969 | A1* | 6/2018 | Nakamura ........... G02B 21/025 |
| 2020/0288946 | A1 | 9/2020 | Takahashi |

FOREIGN PATENT DOCUMENTS

| | | |
|---|---|---|
| EP | 2749929 B1 | 10/2019 |
| WO | 1995009560 A1 | 4/1995 |
| WO | 2017119188 A1 | 7/2017 |

OTHER PUBLICATIONS

"SL 130 Slit Lamp—Maximum quality for optimum performance", 2018, 5 pages.
Scienscope, Tilting or fixed optical head, 2018 2 pages.
Scienscope, "E-Series Parallel Zoom Binocular Microscope Systems", 2018, 13 pages.
Roach, L., "Seven Risk Factors for Injury, and Seven Solutions: Ergonomics, Part Two", Eyenet, 2018, pp. 45-46.
NIKON "Microscopy", Basic Microscope Ergonomics, MicroscopyU, 2018 20 pages.
NIKON "Tubes", Microscope Solutions, 2018, 4 pages.
Chams, H., et al., "Frequency and Assortment of Self-Reported Occupational Complaints Among Iranian Ophthalmologists: A Preliminary Survey", MedGenMed, Dec. 13, 2004, 22 pages, 6(4): 1.
Kent, C., "Will ophthalmology Cripple You?" Review of Ophthalmology, Oct. 4, 2011, 21 pages.
Bay Optical "Extended Eyetube", 2018, 2 pages.
Dhimitri, K. C., et al, "Symptoms of Musculoskeletal Disorders in Ophthalmologists", Am J Ophthalmol 2005; pp. 179-181, 139.
Chatterjee, A., et al., "Back Pain in Ophthalmologists", Eye, 1994, pp. 473-474, 8.
"Accento Ergo tube", 2018, 1 page.
Miller, M. N., et al., "The Painful Truth: Physicians are not Invincible", Southern Medical Journal, Oct. 2000, pp. 966-973, vol. 93, No. 10.
Sivak-Callcott, J., et al., "A Survey Study of Occupational Pain and Injury in Ophthalmic Plastic Surgeons", Ophthal Plast Reconstr Surg, 2011, 5 pages, vol. 27, No. 1.
Invitation To Pay Additional Fees received in a corresponding foreign application dated Apr. 5, 2022, 3 pages.
Supplementary European Search Report dated Nov. 12, 2024 received in a corresponding foreign application, namely European Patent Application No. 22746648.9, 9 pages.

* cited by examiner

OPHTHALMIC INSTRUMENT EYEPIECE EXTENDER

CROSS REFERENCE TO RELATED APPLICATION

This application claims priority under 35 U.S.C. § 119 to provisional patent application U.S. Ser. No. 63/143,389, filed Jan. 29, 2021, the entire contents and appendix of which are incorporated herein by reference.

FIELD

The disclosure relates to ophthalmic instruments, such as e.g. a slit lamp, a microscope, including a surgical microscope, a standard table-top scientific microscope and the like, and an eyepiece extender for such instruments to ameliorate ergonomics.

BACKGROUND

Use of current ophthalmic instruments can lead to physical ailments due to the position the examining doctor or other medical professional is forced to assume in order to operate the instrument. Among such instruments in this regard include surgical microscopes and slit lamps. Representatively, a slit lamp is a microscope which is able to provide a three-dimensional examination of the eye. For this purpose, the slit lamp uses a thin elongated beam of light whose height and/or width can be adjusted to achieve certain views in concert, as needed, with changes of the angle at which the light impinges the eye in order to discern details of the anatomy thereof. The light source can be above or below the slit lamp instrument, and can be of different types, including diffuse illumination, direct focal illumination, specular reflection, indirect lateral illumination, trans-illumination, and sclerotic scatter. Different light filters are also known which can enhance the visualization of certain anatomical features as desired.

The typical slit lamp has at least two magnifications, low magnification and high magnification, sometimes conventionally notated on the slit lamp as e.g. 1× and 1.6× respectively, which facilitates the eye examination. In practice, the eyepiece for a slit lamp is binocular to enable stereoscopic examination of the eye, and, by conventional design, is located close to the instrument. This close proximity of the eyepiece to the instrument requires the user, e.g. a medical professional, to bend or lean at an awkward angle often for significant periods of time, which, over the course of multiple patients and years of practice, can cause chronic and painful back problems. Moreover, the chance of contagion is increased the closer the medical professional is to an infected patient when using known slit lamps. There is thus a need for an extended eyepiece for such instruments which will allow comfortable, protracted use by the medical professional which reduces back and other ailments caused by conventional slit lamps, and which provides a measure of increased safety when used with infected patients.

SUMMARY

In one practice, the disclosure is directed to an eyepiece extender for an ophthalmic instrument, such as a slit lamp, comprising, in the direction of a light beam from an object (e.g. the eye of a patient) to an image (e.g. the eye of the patient as presented to the medical professional by the instrument) (i) a front afocal relay lens group; and (ii) a rear afocal relay lens group, the rear afocal relay group being substantially identical to the front afocal relay lens group and disposed in reverse sequence to the first afocal relay lens group. In one embodiment, the front afocal relay lens group comprises identical components as the rear afocal relay lens group only disposed in a reverse symmetric configuration.

DETAILED DESCRIPTION

The following detailed description of embodiments of the disclosure is made with reference to the accompanying figures. This is for purposes of convenience only and is not restrictive of the scope of the disclosure and the practice thereof. Explanation of related functions or constructions known in the art are omitted for the sake of brevity.

Figure 1A:
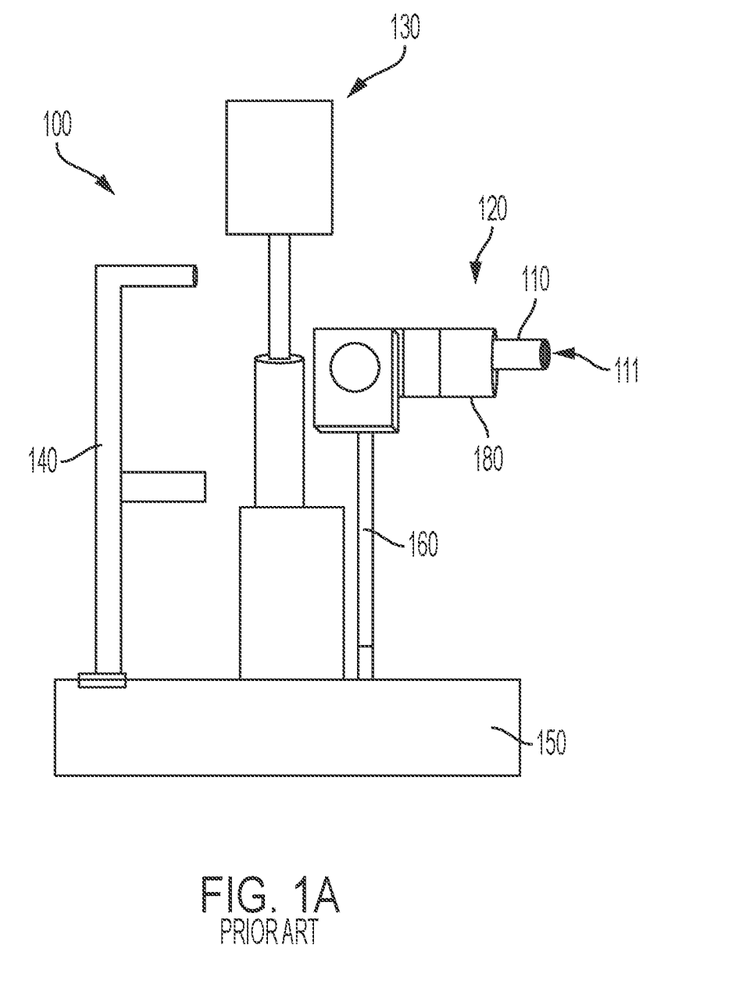
FIG. 1A is a side view of a generic slit lamp microscope having a binocular eyepiece as known in the prior art.
Figure 1B:
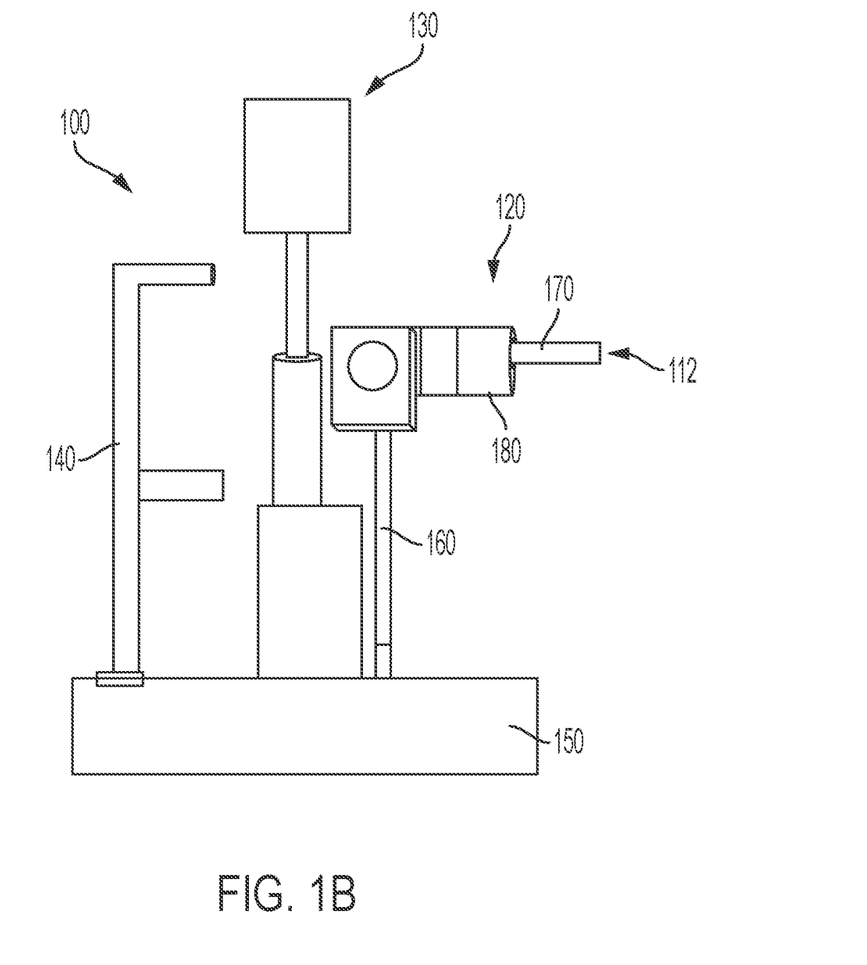
FIG. 1B is a side view of a generic slit lamp microscope employing an embodiment of the eyepiece extender of the disclosure.
Figure 2A:
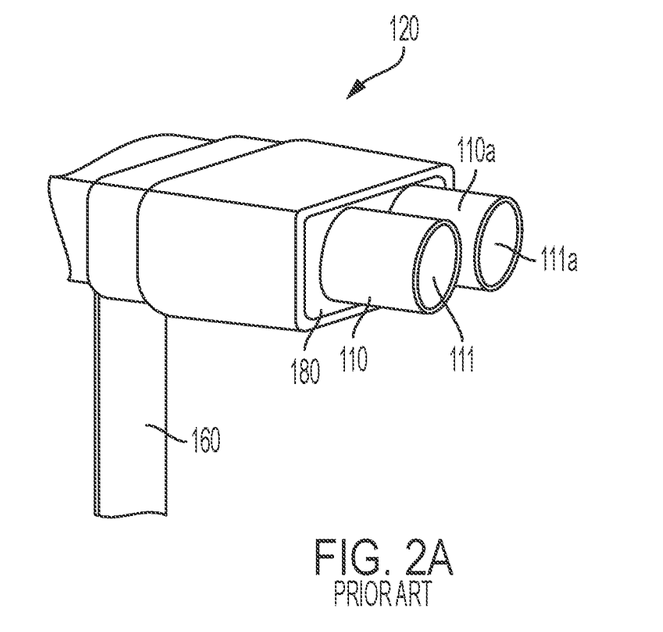
FIG. 2A is a partial close up perspective view of a portion of the slit lamp having the binocular eyepiece of FIG. 1A.

Referring to FIGS. 1A and 2A, thereat is a generalized depiction of a slit lamp microscope 100 as known in the art comprising binocular eyepieces 110 and 110a with viewing ends 111 and 111a, microscope system 120, support arm 160, table 150, and light source system 130 which projects a slit pattern light to an eye of a patient whose face is positioned in headrest 140. The slit lamp microscope 100 has at least two magnifications, low and high, which can vary, for example, from 1× to 1.6×, or 10× to 25×, and the like, respectively. It will be understood to the artisan that the slit lamp depicted is a generalization and that other slit lamp designs and configurations, including without limitation variations of the location of and type light system and the like, are contemplated within the scope of this disclosure. As aforesaid, prior art slit lamps as shown in FIGS. 1A and 2A can cause debilitating effects over time to the back of the user of the lamp due to the design of binocular eyepieces 110, 110a which require the user to lean or bend toward the viewing ends 111, 111a to view the image of the patient eye. The instant disclosure provides binocular eyepiece extenders, 170, 170a as shown in FIGS. 1B and 2B, which allows the user to adopt a more upright posture and thereby reduces the need for the user to lean unduly toward viewing ends 112, 112a, thus ameliorating back problems.

Figure 2B:
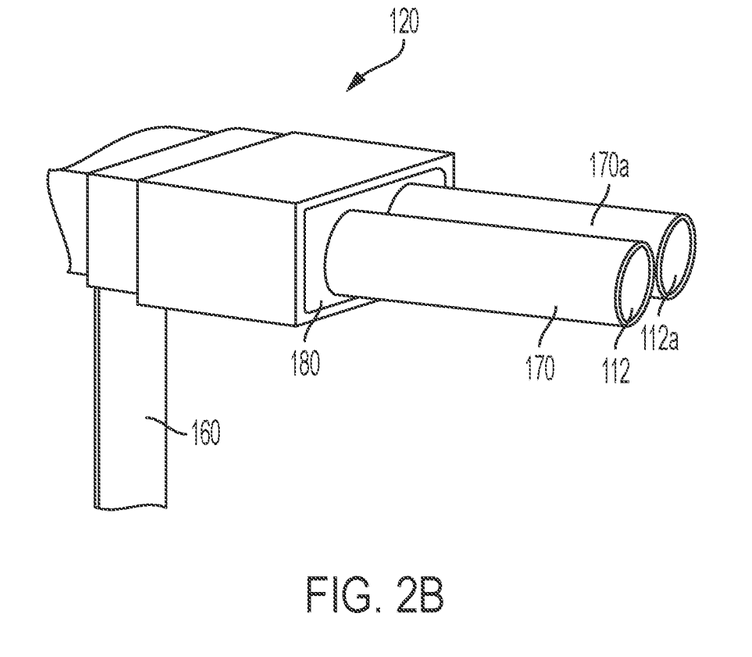
FIG. 2B is a partial close up perspective view of the slit lamp employing the eyepiece extender of FIG. 1B.
Figure 3:
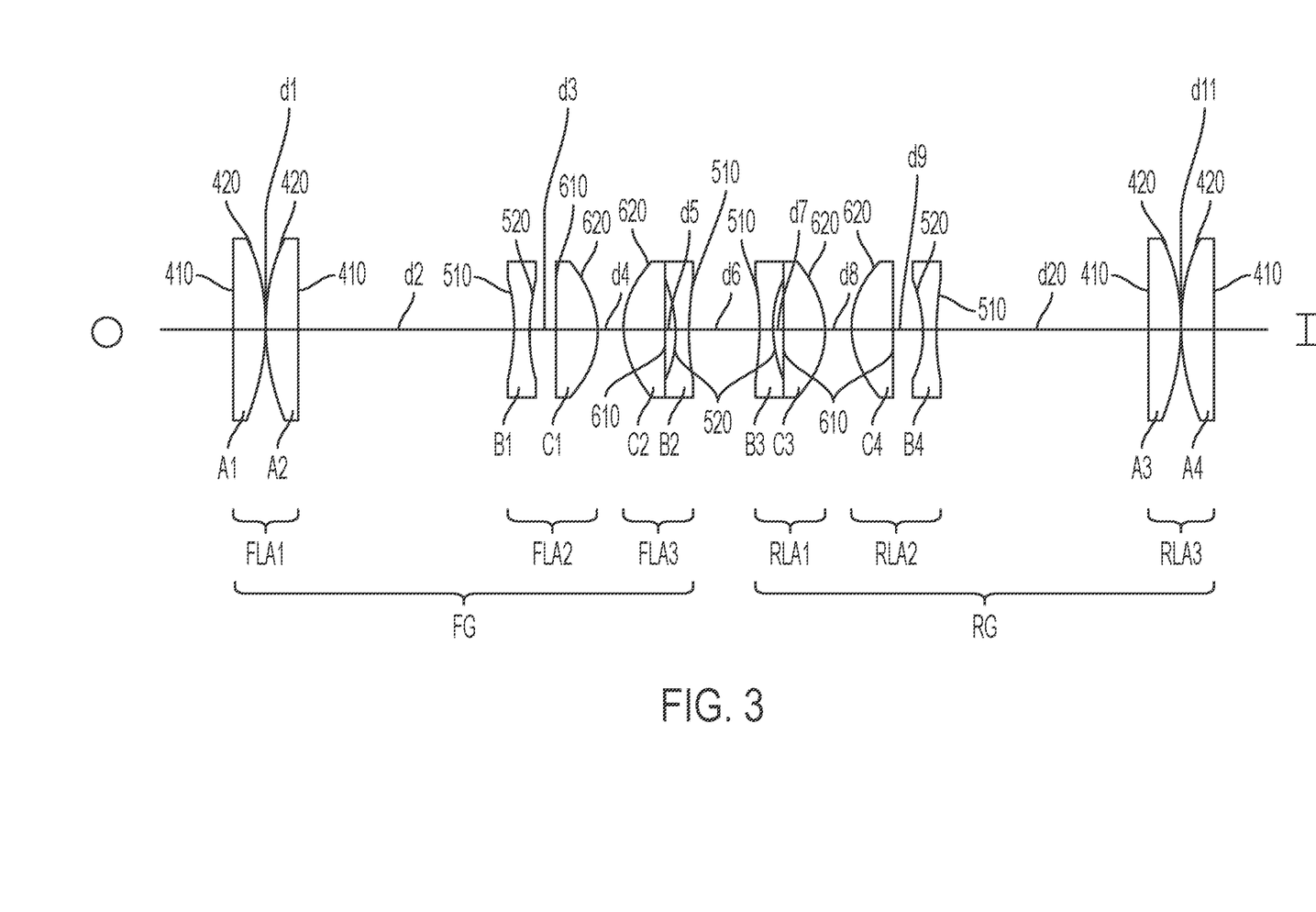
FIG. 3 is a sectional view the lens groups comprising an embodiment of the eyepiece extender of the disclosure.
Figure 4:
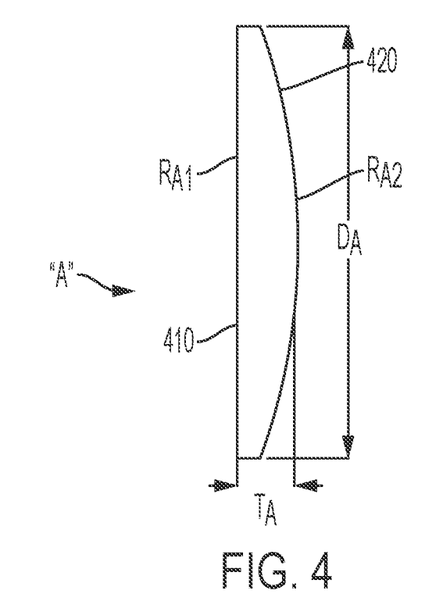
FIG. 4 is a sectional view of an embodiment of lens element "A" (i.e. A1, A2, A3, and A4) in FIG. 3.

In one practice, the eyepiece extender 170, 170a as described herein can be separate pieces (as shown in FIG. 2B) or can be integrally formed as unitary piece (not shown) and made of plastic or metal or other suitable material of construction. In one embodiment, the eyepiece extenders 170, 170a, can be connected to housing 180 of the slit lamp by conventional means such as, without limitation, by sliding them into housing 180 where they are secured by a friction or press fit; other means of connection are contemplated, such as securing the eyepiece extenders to fittings or mounts on the housing that are designed to receive the binocular eyepieces. In one practice, the binocular eyepieces comprise binocular eyepiece extenders 170, 170a that each individually are of generally the same size and shape, e.g. cylindrical outer shape, and each individually comprise, in one embodiment, the lens elements A, B, and C, as arranged in FIG. 3 and as defined herein. The particulars of the lens elements are as follows:

The "A" lens element, four of which appear in FIG. 3 denoted A1, A2, A3, and A4, is shown at FIG. 4. Lens element A is a plano-convex lens having a flat side 410, flat side 410 having a radius of curvature $R_{A1}$ of infinity (plano), and a convex side 420, the convex side 420 having a radius of curvature, $R_{A2}$, of between 23.9400 to 23.9410 mm, e.g. 23.9406 mm. Lens element A has a diameter DA of 20 mm-0.05 mm/+0.000 mm, and has a thickness TA at its center of 3.5 mm±0.1 mm. The edges of lens element A may optionally be beveled at 45° to 1 mm maximum face width. Lens element A has an index of refraction, $N_d$, of about 1.7550±0.001, including 1.755002, and an Abbe number, $V_d$, of about 52.33±0.5233. Lens element A comprises a low dispersion glass, such as without limitation, crown glass, e.g. lanthanum crown glass, including lanthanum crown glass commercially available as H-LAK53A.

Figure 5:
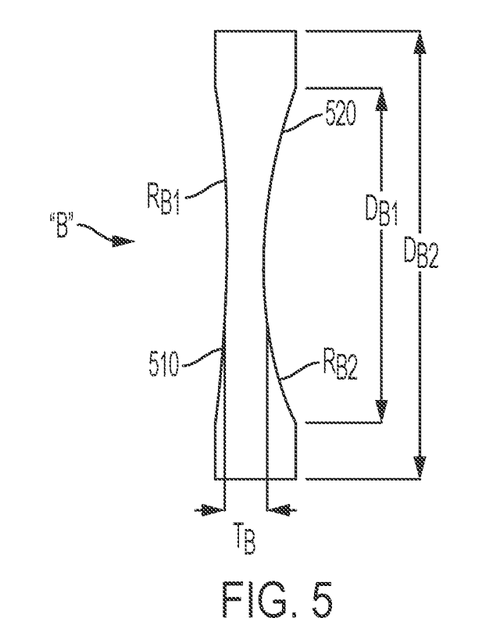
FIG. 5 is a sectional view of an embodiment of lens element "B" (i.e. B1, B2, B3, and B4) in FIG. 3.

The "B" lens element, denoted in FIG. 3 as B1, B2, B3, and B4, is shown at FIG. 5. Lens element B is an asymmetrical double concave lens having different radii of curvature on either side. As shown in FIG. 5, is an embodiment of lens element B having a first concave side 510 having a radius of curvature $R_{B1}$ and a second concave side 520 having a radius of curvature $R_{B2}$, where $R_{B1}$ is the greater radius of curvature, and $R_{B2}$ is the lesser radius of curvature ($R_{B1}$>$R_{B2}$) and where, in one practice, $R_{B1}$ is between 27.2150 to 27.2160 mm, e.g. 27.2156 mm; and $R_{B2}$ is between 16.6710 to 16.6720 mm, e.g. 16.6719 mm. Lens element B has a diameter $D_{B1}$ for the concavity on each side of 11.2 mm with ±tolerances of −0.05 mm/+0.000 mm, and an outer diameter $D_{B2}$ of the lens of 15.00 mm with tolerances of −0.05 mm/+0.000 mm. Lens element B has center thickness, TB, of 1.5 mm with tolerances of −0.1 mm/+0.000 mm. The edges of lens element B may optionally be beveled at 45° to 1 mm maximum face width. Lens element B has an index of refraction, $N_d$, of about 1.8467±0.001, including 1.846669, and an Abbe number, $V_d$, of about 23.83±0.2383. Lens element B comprises a high dispersion glass, such as without limitation, flint glass, e.g. dense flint glass, including dense flint glass commercially available as ZF52.

Figure 6:
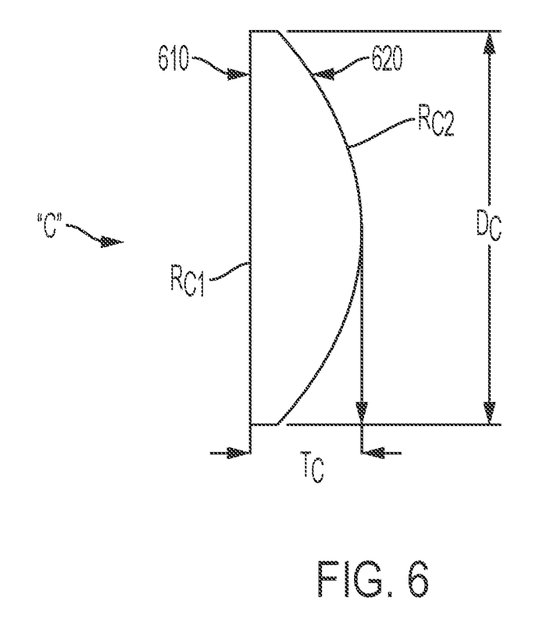
FIG. 6 is a sectional view of an embodiment of lens element "C" (i.e. C1, C2, C3, and C4) in FIG. 3.

The "C" lens element, denoted in FIG. 3 as C1, C2, C3, and C4, is shown at FIG. 6. Lens element B is a meniscus lens having a concave side and a convex side. As shown in FIG. 6, is an embodiment of lens element C having a concave side 610 having a radius of curvature $R_{C1}$ and a convex side 620 having a radius of curvature $R_{C2}$. In one practice concave radius $R_{C1}$ is between about 332.9400 to 332.9410 mm, e.g. 332.9480 mm, and convex radius $R_{C2}$ is between 9.9500 to 9.9510 mm, e.g. 9.9502 mm. Lens element C has a diameter Dc 15 mm with tolerances of −0.05 mm/+0.000 mm. Lens element C has center thickness, Tc, of 4.5 mm±-0.1 mm. The edges of lens element C may optionally be beveled at 45° to 1 mm maximum face width. Lens element C has an index of refraction, $N_d$, of about 1.7550±0.001, including 1.755002, and an Abbe number $V_d$, of about 52.33±0.5233. Lens element C comprises a low dispersion glass, such as without limitation, crown glass, e.g. lanthanum crown glass, including lanthanum crown glass commercially available as H-LAK53A. In one practice, lens element C comprises the same glass as lens element A; in another practice, the glass of lens elements A and C are each independent but within the parameters herein given. Glass meeting the requirements of lens elements A, B, and C, such as H-LAK53A and ZF52, are commercially obtainable from Ohara Corporation and Schott AG.

In a preferred practice, lens elements A, B, and C have the following parameters as above defined:

| Lens Element A | |
|---|---|
| Radii of Curvature (mm): | $R_{A1}$ = infinity (plano) |
| | $R_{A2}$ = 23.9400 to 23.9410 |
| Diameter (mm): | $D_A$ = 20 + 0/−0.05 |
| Thickness (mm): | $T_A$ = 3.5 ± 0.1 |
| Index of Refraction: | $N_d$ = 1.7550 ± 0.001 |
| Abbe Number: | $V_d$ = 52.33 ± 0.5233 |
| Material: | lanthanum crown glass |

| Lens Element B | |
|---|---|
| Radii of Curvature (mm): | $R_{B1}$ = 27.2150 to 27.2160 |
| | $R_{B2}$ = 16.6710 to 16.6720 |
| Diameter (mm): | $D_{B1}$ = 11.2 + 0/−0.05 |
| | $D_{B2}$ = 15.00 + 0/−0.05 |
| Thickness (mm): | $T_B$ = 1.5 + 0/−0.1 |
| Index of Refraction: | $N_d$ = 1.8467 ± 0.001 |
| Abbe Number: | $V_d$ = 28.83 ± 0.2383 |
| Material: | dense flint glass |

| Lens Element C | |
|---|---|
| Radii of Curvature (mm): | $R_{C1}$ = 332.9400 to 332.9410 |
| | $R_{C2}$ = 9.9500 to 9.9510 |
| Diameter (mm): | $D_C$ = 15 + 0/−0.05 |
| Thickness (mm): | $T_C$ = 4.5 + 0/−0.1 |
| Index of Refraction: | $N_d$ = 1.7550 ± 0.001 |
| Abbe Number: | $V_d$ = 52.33 ± 0.5233 |
| Material: | lanthanum crown glass |

An embodiment of the eyepiece extender of the disclosure in sectional view showing the lens elements and arrangement is depicted FIG. 3 is discussed herein in the direction of an optical beam path going from object O (e.g. the eye of a patient) to image I (e.g. the image of the patient eye as seen by the user of the ophthalmic instrument, e.g. at the viewing end of the eyepiece extender), and comprises a front afocal relay lens group FG and a rear afocal relay lens group RG, wherein, as shown in FIG. 3, the front afocal relay lens group FG and the rear afocal relay lens group RG are substantially identical in terms of lens elements and distancing but whose lens elements are in reverse sequence thereby providing a symmetrical arrangement between FG and RG. As used herein, the terms "about" and "substantially identical" intend sizes, shapes, distances, arrangements, and the like that can vary within the error tolerance levels given herein while still preserving image fidelity at both the high and low magnifications, e.g. the fidelity of the image at high and low magnification are distortion free and color corrected as understood in the art. Similarly, the distances between lenses and lens radii disclosed herein can be varied within the tolerances given as long as the image fidelity is preserved at both the high and low magnifications, e.g. the fidelity of the image at high and low magnification are distortion free and color corrected as understood in the art.

In the embodiment of FIG. 3, the front afocal relay lens group FG comprises, in the direction of an optical beam path going from object O to image I, (i) a first front lens assembly FLA1 comprising a first plano-convex lens element A1 and a second plano-convex lens element A2, arranged so that the convex surface 420 of A1 and the convex surface 420 of A2, face each other and are separated by distance d1 (all distances, d, discussed in regard to FIG. 3 are air gap); (ii) a second front lens assembly FLA2 comprising a first asymmetrical double concave lens element B1 having a greater radius of curvature ($R_{B1}$) on one side 510 and a lesser radius of curvature ($R_{B2}$) on the other side 520, and a first meniscus lens element C1, wherein the concave surface 610 of the first meniscus lens element C1 faces the side 520 of the first asymmetrical double concave lens element B1 having the lesser radius of curvature ($R_{B2}$) and separated by distance d3; and (iii) a third front lens assembly FLA3 comprising a second meniscus lens element C2 and a second asymmetrical double concave lens element B2 having a greater radius of curvature ($R_{B1}$) on one side 510 and a lesser radius of curvature ($R_{B2}$) on the other side 520, wherein the concave surface 610 of the second meniscus lens element C2 faces the side 520 of the first asymmetrical double concave lens element B2 having the lesser radius of curvature ($R_{B2}$) and separated by distance d5. As shown in FIG. 3, FLA1 and FLA 2 are separated by a distance d2, and FLA2 is separated from FLA3 by a distance d4.

Continuing with FIG. 3, the rear afocal relay lens group RG comprises, in the direction from O to I, (iv) a first rear lens assembly RLA1 comprising a third asymmetrical double concave lens element B3 having a greater radius of curvature ($R_{B1}$) on one side 510 and a lesser radius of curvature ($R_{B2}$) on the other side 520, and a third meniscus lens element C3, wherein the concave surface 610 of the third meniscus lens element C3 faces the side 520 of the third asymmetrical double concave lens element B3 having the lesser radius of curvature ($R_{B2}$) and separated by distance d7; (v) a second rear lens assembly RLA2 comprising a fourth meniscus lens element C4 and a fourth asymmetrical double concave lens element B4 having a greater radius of curvature ($R_{B1}$) on one side 510 and a lesser radius of curvature ($R_{B2}$) on the other side 520, wherein the concave surface 610 of the fourth meniscus lens element C4 faces the side 520 of the fourth asymmetrical double concave lens element B4 having the lesser radius of curvature ($R_{B2}$) and separated by distance d9; and (vi) a third rear lens assembly RLA3 comprising a third plano-convex lens element A3 and a fourth plano-convex lens element A4, arranged so that the convex surface 420 of the third plano-convex lens element A3 and the convex surface 420 of the fourth plano-convex lens element A4 (420), face each other and are separated by distance d11.

In the practice shown in FIG. 3, RLA1 and RLA 2 are separated by a distance d8, and RLA2 is separated from RLA3 by a distance d10. FLA3 is separated from RLA1 by a distance d6. In an embodiment where the lens arrangement shown in FIG. 3 is barreled by means known in the art, a stop, also as known in the art, can be disposed between FLA3 and RLA1, e.g. about midway along distance d6. Also as shown in the embodiment of FIG. 3, FLA1 is separated from FLA2 by distance d2 as measured from A2 side 410 to B1 side 510; FLA2 is separated from FLA3 by distance d4 as measured from C1 side 620 to C2 side 620; FLA3 is separated from RLA1 by distance d6 as measured from B2 side 510 to B3 side 510; RLA1 is separated from RLA2 by distance d8 as measured from C3 side 620 to C4 side 620; and RLA2 is separated from RLA3 by distance d10 as measured from B4 side 510 to A3 side 410.

Representative distances for $d_{11}$-$d_{11}$ in FIG. 3 are delineated below:

Distances (air gap), d, in FIG. 3
d1=0.050 mm±0.10 mm
d2=23.625 mm±0.10 mm
d3=3.100 mm±0.10 mm
d4=3.042 mm±0.10 mm
d5=1.100 mm±0.10 mm
d6=7.866 mm±0.10 mm
d7=1.100 mm±0.10 mm
d8=3.042 mm±0.10 mm
d9=3.100 mm±0.10 mm
d10=23.625 mm±0.10 mm
d11=0.050 mm±0.10 mm In another practice, the eyepiece extender of the disclosure consists essentially of the lens groups as described and arranged in FIG. 3. In still another practice, the eyepiece extender of the disclosure consists of the lens groups as described and arranged in FIG. 3. The lens groups of FIG. 3 can be barreled by methods know in the art, the overall length of the extender being, in one embodiment, approximately 6 inches (approximately 15-16 cm, e.g. 15.24 cm), which additional distance provides ergonomic relief to the user of the slit lamp.

In another practice, the disclosure is directed to a slit lamp microscope comprising a light source system for projecting a slit-pattern light to an eye of a patient to illuminate the eye of the patient and a microscope system comprising binocular eyepiece extenders, each eyepiece extender individually comprising a viewing end through which a user of the microscope system can observe the illuminated eye of the patient. The slit lamp can further comprise an objective lens element or system, as known in the art, disposed between the eye of the patient and the binocular eyepiece extenders, and a magnification changing system disposed between the objective lens and the binocular eyepiece extenders, and can comprise digital or other photographic and video systems to record the image of the patient's eye, all as known in the art, see, e.g. FIGS. 1A, 2A. In this practice, the slit lamp comprises first and second eyepiece extenders, each of the first and the second eyepiece extenders individually comprising, in the direction from the eye of the patient to the viewing ends (from object to image), a front afocal relay lens group; and a rear afocal relay lens group, the rear afocal relay group being substantially identical to the front afocal relay lens group and disposed in reverse sequence to the first afocal relay lens group as described herein. In one embodiment, the first and second eyepiece extenders are separate pieces or are integrally formed as a single piece. In one practice, each of the first and second eyepiece extenders comprises the lens groups as described for and as arranged in FIG. 3.

In one embodiment, the first and second eyepiece extenders are separate pieces or are integrally formed as a single piece. In one practice, each of the first and second eyepiece extenders comprises the lens groups as described for and as arranged in FIG. 3.

While the disclosure has been shown and described with reference to certain embodiments, it will be understood by those of skill in the art that various changes in and from the details may be made without departing from the scope of the present disclosure and its equivalents.

What is claimed is:

1. An eyepiece extender for an ophthalmic instrument comprising, in the direction of an optical beam path from an object to an image:
   (a) a front afocal relay lens group comprising:
      a first front lens assembly comprising a first plano-convex lens element and a second plano-convex lens element arranged so that the convex surface of the first plano-convex lens element and the convex surface of the second plano-convex lens element face each other;
      a second front lens assembly comprising a first asymmetrical double concave lens element having a greater radius of curvature on one side and a lesser radius of curvature on the other side, and a first meniscus lens element, wherein the concave surface of the first meniscus lens element faces the side of the first asymmetrical double concave lens element having the lesser radius of curvature;
      a third front lens assembly comprising a second meniscus lens element and a second asymmetrical double concave lens element having a greater radius of curvature on one side and a lesser radius of curvature on the other side, wherein the concave surface of the second meniscus lens element faces the side of the first asymmetrical double concave lens element having the lesser radius of curvature; and
   (b) a rear afocal relay lens group, the rear afocal relay group being substantially identical to the front afocal relay lens group and disposed in reverse sequence to the first afocal relay lens group.

2. The eyepiece extender of claim 1 wherein the first and second plano-convex lens elements are substantially identical.

3. The eyepiece extender of claim 1 wherein the first asymmetrical double concave lens element and the second asymmetrical double concave lens element are substantially identical.

4. The eyepiece extender of claim 1 wherein the first meniscus lens element and the second meniscus lens element are substantially identical.

5. The eyepiece extender of claim 1 wherein the first and second plano-convex lens elements, and the first meniscus lens element and the second meniscus lens element each individually comprise low dispersion glass; and the first asymmetrical double concave lens element and the second asymmetrical double concave lens element each individually comprise high dispersion glass.

6. The eyepiece extender of claim 1 wherein the rear afocal relay lens group comprises, in the direction of the optical beam path from the object to the image:
   a first rear lens assembly comprising a third asymmetrical double concave lens element having a greater radius of curvature on one side and a lesser radius of curvature on the other side and a third meniscus lens element wherein the concave surface of the third meniscus lens element faces the side of the third asymmetrical double concave lens element having the lesser radius of curvature;
   a second rear lens assembly comprising a fourth meniscus lens element and a fourth asymmetrical double concave lens element having a greater radius of curvature on one side and a lesser radius of curvature on the other side, wherein the concave surface of the fourth meniscus lens element faces the side of the fourth asymmetrical double concave lens element having the lesser radius of curvature; and
   a third rear lens assembly comprising a third plano-convex lens element and a fourth plano-convex lens element, arranged so that the convex surface of the third plano-convex lens element and the convex surface of the fourth plano-convex lens element face each other.

7. The eyepiece extender of claim 6 wherein the third and fourth plano-convex lens elements are substantially identical.

8. The eyepiece extender of claim 6 wherein the asymmetrical third asymmetrical double concave lens element and the fourth asymmetrical double concave lens element are substantially identical.

9. The eyepiece extender of claim 6 wherein the third meniscus lens element and the fourth meniscus lens element are substantially identical.

10. The eyepiece extender of claim 6 wherein the third and fourth plano-convex lens elements, and the third meniscus lens element and the fourth meniscus lens element each individually comprise low dispersion glass; and the third asymmetrical double concave lens element and the fourth asymmetrical double concave lens element each individually comprise high dispersion glass.

11. The eyepiece extender of claim 6 wherein the first, second, third, and fourth plano-convex lens elements are substantially identical; the first, second, third, and fourth asymmetrical double concave lens elements are substantially identical; and the first, second, third, and fourth meniscus lens elements are substantially identical.

12. The eyepiece extender of claim 11 wherein the convex surfaces of the first, second, third, and fourth plano-convex lens elements each individually have a radius of curvature ($R_{A2}$) of about 23.941.

13. The eyepiece extender of claim 11 wherein the lesser radius of curvature for each of the first, second, third, and fourth asymmetrical double concave lens elements is individually about 16.672 ($R_{B2}$); and the greater radius of curvature ($R_{B1}$) for each of the first, second, third, and fourth asymmetrical double concave lens elements is individually about 27.216.

14. The eyepiece extender of claim 11 wherein the first, second, third, and fourth meniscus lens elements each individually have concave surface with a radius of curvature ($R_{C1}$) of about 332.948, and a convex surface with a radius of curvature ($R_{C2}$) of about 9.950.

15. The eyepiece extender of claim 1 wherein the front afocal relay lens group and the rear afocal relay lens group are axially disposed within a cylindrical barrel, the cylindrical barrel having at least one end adapted for attachment to an eyepiece of an ophthalmic instrument.

16. The eyepiece extender of claim 15 wherein the ophthalmic instrument comprises a slit lamp microscope or a microscope.

17. An eyepiece extender for a slit lamp microscope comprising, in the direction of an optical beam path from an object to an image:
   (a) a front afocal relay lens group (FG) comprising, in the direction of the optical beam path from the object to the image:
      (i) a first front lens assembly (FLA1) comprising a first plano-convex lens element and a second plano-convex lens element arranged so that the convex surface of the first plano-convex lens element and the convex surface of the second plano-convex lens element face each other and are separated by a distance of d1;

(ii) a second front lens assembly (FLA2) separated from FLA1 by a distance d2 and comprising a first asymmetrical double concave lens element having a greater radius of curvature on one side and a lesser radius of curvature on the other side, and a first meniscus lens element, wherein the concave surface of the first meniscus lens element faces the side of the first asymmetrical double concave lens element having the lesser radius of curvature and is separated by a distance d3; and (iii) a third front lens assembly (FLA3) separated from FLA2 by a distance d4 and comprising a second meniscus lens element and a second asymmetrical double concave lens element having a greater radius of curvature on one side and a lesser radius of curvature on the other side, wherein the concave surface of the second meniscus lens element faces the side of the first asymmetrical double concave lens element having the lesser radius of curvature and is separated by a distance d5; and wherein:

(b) a rear afocal relay lens group (RG) comprising, in the direction of the optical beam path from the object to the image:

(i) a first rear lens assembly (RLA1) separated from FLA3 by a distance of d6 and comprising a third asymmetrical double concave lens element having a greater radius of curvature on one side and a lesser radius of curvature on the other side and a third meniscus lens element wherein the concave surface of the third meniscus lens element faces the side of the third asymmetrical double concave lens element having the lesser radius of curvature and are separated by a distance d7;

(ii) a second rear lens assembly (RLA2) separated from RLA1 by a distance d8 and comprising a fourth meniscus lens element and a fourth asymmetrical double concave lens element having a greater radius of curvature on one side and a lesser radius of curvature on the other side, wherein the concave surface of the fourth meniscus lens element faces the side of the fourth asymmetrical double concave lens element having the lesser radius of curvature and separated by a distance d9; and (iii) a third rear lens assembly (RLA3) separated from RLA2 by a distance d10 and comprising a third plano-convex lens element and a fourth plano-convex lens element, arranged so that the convex surface of the third plano-convex lens element and the convex surface of the fourth plano-convex lens element face each other and are separated by a distance d11, wherein:

the first and second plano-convex lens elements, the first meniscus lens element and the second meniscus lens element, the third and fourth plano-convex lens elements, and the third meniscus lens element and the fourth meniscus lens element each individually comprise low dispersion glass comprising an index of refraction, $N_d$, of 1.7550±0.001 and an Abbe number, $V_d$, of 52.33±0.5233; and the first asymmetrical double concave lens element, the second asymmetrical double concave lens element, the third asymmetrical double concave lens element, and the fourth asymmetrical double concave lens element each individually comprise high dispersion glass comprising an index of refraction, $N_d$, of 1.8467±0.001 and an Abbe number, $V_d$, of 23.83±0.2383, and wherein the convex surfaces of the first, second, third, and fourth plano-convex lens elements each individually have a radius of curvature ($R_{A2}$) of about 23.941; the lesser radius of curvature for each of the first, second, third, and fourth asymmetrical double concave lens elements is individually about 16.672 ($R_{B2}$); and the greater radius of curvature ($R_{B1}$) for each of the first, second, third, and fourth asymmetrical double concave lens elements is individually about 27.216; the first, second, third, and fourth meniscus lens elements each individually have concave surface with a radius of curvature ($R_{C1}$) of about 332.948, and a convex surface with a radius of curvature ($R_{C2}$) of about 9.950, and wherein d1=0.050 mm±0.10 mm
d2=23.625 mm±0.10 mm
d3=3.100 mm±0.10 mm
d4=3.042 mm±0.10 mm
d5=1.100 mm±0.10 mm
d6=7.866 mm±0.10 mm
d7=1.100 mm±0.10 mm
d8=3.042 mm±0.10 mm
d9=3.100 mm±0.10 mm
d10=23.625 mm±0.10 mm
d11=0.050 mm±0.10 mm.

18. A slit lamp microscope comprising:
a light source system for projecting a slit-pattern light to an eye of a patient to illuminate the eye of the patient;
a microscope system comprising:
first and second eyepiece extenders, each individually comprising a viewing end through which a user of the microscope system can observe the illuminated eye of the patient, the first and the second eyepiece extenders each individually comprising, in the direction from the eye of the patient to the viewing end, a front afocal relay lens group; and a rear afocal relay lens group, the rear afocal relay group being substantially identical to the front afocal relay lens group and disposed in reverse sequence to the first afocal relay lens group.

19. The slit lamp microscope of claim 18 wherein the first and second eyepiece extenders are separate pieces or are integrally formed as a single piece.

20. The slit lamp microscope of claim 18 wherein the microscope system further comprises an objective lens disposed between the eye of the patient and the first and the second eyepiece extenders.

21. The slit lamp microscope of claim 20 further comprising a magnification changing system disposed between the objective lens and the first and the second eyepiece extenders.

22. The slit lamp microscope of claim 18 wherein:
(a) the front afocal relay lens group comprises, in the direction from the eye of the patient to the viewing ends:
(i) a first front lens assembly comprising a first plano-convex lens element and a second plano-convex lens element arranged so that the convex surface of the first plano-convex lens element and the convex surface of the second plano-convex lens element face each other;
(ii) a second front lens assembly comprising a first asymmetrical double concave lens element having a greater radius of curvature on one side and a lesser radius of curvature on the other side, and a first meniscus lens element, wherein the concave surface of the first meniscus lens element faces the side of the first asymmetrical double concave lens element having the lesser radius of curvature; and (iii) a third front lens assembly comprising a second meniscus lens element and a second asymmetrical double concave lens element having a greater radius of curvature on one side and a lesser radius of curvature on the other side, wherein the concave surface of the second meniscus lens element faces the side of the first asymmetrical double concave lens element having the lesser radius of curvature; and wherein:

(b) the rear afocal relay lens group comprises, in the direction from the eye of the patient to the viewing ends:

(i) a first rear lens assembly comprising a third asymmetrical double concave lens element having a greater radius of curvature on one side and a lesser radius of curvature on the other side and a third meniscus lens element wherein the concave surface of the third meniscus lens element faces the side of the third asymmetrical double concave lens element having the lesser radius of curvature;

(ii) a second rear lens assembly comprising a fourth meniscus lens element and a fourth asymmetrical double concave lens element having a greater radius of curvature on one side and a lesser radius of curvature on the other side, wherein the concave surface of the fourth meniscus lens element faces the side of the fourth asymmetrical double concave lens element having the lesser radius of curvature; and (iii) a third rear lens assembly comprising a third plano-convex lens element and a fourth plano-convex lens element, arranged so that the convex surface of the third plano-convex lens element and the convex surface of the fourth plano-convex lens element face each other.

\* \* \* \* \*

UNITED STATES PATENT AND TRADEMARK OFFICE
CERTIFICATE OF CORRECTION

PATENT NO. : 12,196,946 B2
APPLICATION NO. : 17/587182
DATED : January 14, 2025
INVENTOR(S) : Ronald Michael Caronia et al.

Page 1 of 1

It is certified that error appears in the above-identified patent and that said Letters Patent is hereby corrected as shown below:

On the Title Page

Item (73) Assignee should read:
Ronald Michael Caronia, Syosett, NY (US)

Signed and Sealed this
Twenty-fifth Day of March, 2025

Coke Morgan Stewart
*Acting Director of the United States Patent and Trademark Office*